(12) United States Patent
Blight et al.

(10) Patent No.: US 7,273,359 B2
(45) Date of Patent: Sep. 25, 2007

(54) PERISTALTIC IRRIGATION PUMP SYSTEM

(75) Inventors: David D. Blight, Largo, FL (US); Eric N. Stubkjaer, Seminole, FL (US); Joseph A. Fritz, Largo, FL (US)

(73) Assignee: Linvatec Corporation, Largo, FL (US)

( * ) Notice: Subject to any disclaimer, the term of this patent is extended or adjusted under 35 U.S.C. 154(b) by 684 days.

(21) Appl. No.: 10/701,912

(22) Filed: Nov. 5, 2003

(65) Prior Publication Data
US 2005/0095155 A1 May 5, 2005

(51) Int. Cl.
*F04B 43/12* (2006.01)
*F04B 49/08* (2006.01)
*A61M 1/00* (2006.01)

(52) U.S. Cl. .............................. 417/477.13; 417/477.2; 417/44.2; 417/44.7; 417/44.9; 604/153

(58) Field of Classification Search ........... 417/477.13, 417/477.2, 44.3, 477.1, 44.2, 44.7, 44.9; 604/131, 151, 153
See application file for complete search history.

(56) References Cited

U.S. PATENT DOCUMENTS 5,927,956 A * 7/1999 Lim et al. .............. 417/477.13
6,468,059 B2 * 10/2002 Haser et al. ............. 417/477.1

* cited by examiner

*Primary Examiner*—Anthony D. Stashick
*Assistant Examiner*—Jessica L Frantz
(74) *Attorney, Agent, or Firm*—Gene Warzecha

(57) ABSTRACT

A peristaltic pump tubing system for use with a peristaltic pump roller assembly in a surgical procedure. The system comprises a uniquely shaped disposable cassette for retaining tubing to be used during the procedure and a uniquely shaped cassette receiving station situated adjacent the roller assembly. The cassette comprises a frame for holding the tube in a loop shape for engagement with the peristaltic rollers. The frame supports a one-sided pressure transducer to indicate the pressure within the tube. The cassette receiving station includes a sensor for engaging the one-sided pressure transducer and is situated adjacent the rollers of the peristaltic pump on the pump housing. A retaining bracket cooperates with the inherent resiliency of the tubing loop to hold the tubing in place against the rollers.

3 Claims, 18 Drawing Sheets

PERISTALTIC IRRIGATION PUMP SYSTEM

BACKGROUND OF THE INVENTION

1. Field of the Invention

The invention relates generally to peristaltic irrigation and distension pumps and tubing sets for use therewith. More particularly, the invention relates to an irrigation and distension pump system for surgical use, the system utilizing a tube set having a tubing cassette which holds a looped tube adjacent peristaltic rollers.

2. Description of the Prior Art

Powered pumps are frequently used in medical and surgical applications in order to pump various fluids during surgical procedures. The fluids are conveyed from a fluid source to a patient and ultimately to a fluid drain via a pump and various inflow and outflow tubes which pass fluid appropriately. Numerous system designs are known by which the tubing used with the pumps may be configured into surgical tube sets adapted for various applications (arthroscopy, laparoscopy, irrigation, etc.). The tube sets may be coded to identify the procedure for which they are designed and can be relatively easily engaged with the pump and other components. With respect to peristaltic pumps in particular, these designs generally utilize a cassette in the form of a molded housing which retains a portion of the tubing so that the engagement of the tubing with the peristaltic pump simply requires the attachment of the cassette adjacent the peristaltic pump roller assembly rather than the laborious process of threading a tube around the roller assembly and securing it in place.

One type of tubing cassette is shown in U.S. Pat. No. 5,460,490 (Carr et al.), assigned to the assignee hereof and incorporated by reference herein. This patent shows a cassette in the form of a molded block having various channels for holding a tube in a predetermined U-shaped orientation in the plane of rotation of the peristaltic pump roller assembly. The cassette is retained adjacent the roller assembly by a cam device which presses the cassette against the front panel of the peristaltic pump housing and holds the tube firmly against the roller assembly without a raceway backing plate. This device is relatively complex and requires more manipulation of the cassette than is desired in certain surgical applications. Additionally, this device requires the use of a track or race to support the tube as it engages the rollers.

Another type of "cassette" is shown in U.S. Pat. No. 5,133,650 (Sunderland et al.) in which the tubing is provided with various fixed molded components which are attachable to complementarily shaped recesses in the pump housing and a pivotable swing arm. The latter may then be swung into place in order to stretch the tube about the peristaltic pump roller assembly. This device is really a two-piece device as opposed to a one-piece cassette and is, therefore, not strictly a cassette as that term is normally understood. A similar "cassette" device is used without a swing arm in the Linvatec C7050 Irrigation Console available from Linvatec Corporation, 11311 Concept Boulevard, Largo, Fla. 33773. This device utilizes a peristaltic pump having a pump roller assembly situated adjacent fixed tube-holding stations designed to be used with a tubing set having fixed molded components secured thereto. The tubing set is used by first placing one of the molded components into one of the tube-holding stations adjacent the roller assembly, then stretching the tube around the roller assembly and securing the other molded component in the other tube-holding station. This arrangement holds the tube in generally a U-shape around the peristaltic pump roller assembly as is often done in peristaltic pumps.

Other cassette arrangements are also known in which a one-piece cassette is used with a pair of latching mechanisms in order to hold the tubing cassette in proper position adjacent the peristaltic pump roller assembly. For example, U.S. Pat. No. 5,433,588 (Monk et al) shows a cassette maintained adjacent a peristaltic pump roller assembly by the cooperative action of a pair of spaced locking surfaces, spaced on either side of the rollers. This device operates with a backing plate so that the peristaltic rollers squeeze the tube between the rollers and the backing plate. The device is relatively complex.

Another known disposable cassette for use with a peristaltic pump is shown in U.S. Pat. No. 4,537,561 (Xanthopoulos). The cassette of this device operates without a backing plate and is secured adjacent the pump by a pair of articulating latch arms which hold opposing sides of the cassette adjacent the pump roller assembly station. While this patent makes a reference to a mechanical or electromechanical arrangement utilized to release this locking mechanism, no such arrangement is shown. However, one can reasonably expect it to be relatively complex since the articulating arms must both be moved simultaneously.

Another peristaltic tubing cassette is shown in U.S. Pat. No. 5,927,956 (Lim et al.), assigned to the assignee hereof. The cassette is designed to attach a tubing set to the front panel of a pump housing having a peristaltic roller assembly rotatable in a plane parallel to the front panel of the housing. The cassette shown in this patent is a three-sided enclosure having an open bottom end. The tubing retained in the enclosure is secured on each side of the open end so that when the cassette is slid over the peristaltic rollers and latched into place, the tubing is automatically stretched around the rollers.

Cassette tube sets are easy to use and assure the proper alignment of various tubes with the pump, solenoid actuated valves, pressure sensors, etc. To further simplify a cassette type irrigation pump system, the present invention utilizes a one-sided pressure transducer.

Known prior art cassette tube systems sometimes utilize pressure sensors to provide feedback to the pump to control output pressure. Such systems often measure pressure at a point downstream and near the surgical site. These devices often utilize a separate, air filled pressure sensing line incorporating a balloon-type interface between the main, liquid filled supply tube and air filled pressure line. The liquid being pumped is on one side of the balloon and an air column is on the other side. The pressure of the liquid varies the pressure on the air column which is sensed by a transducer in the pump housing. For such systems to work the end of the tube carrying the air column must be connected to a transducer at the pump.

It is also known to sense pressure at the pump housing. For example, U.S. Pat. No. 5,044,203 (Weist et al.) shows a peristaltic pump tube set with a portion of the tube formed into a flexible tubing cushion having two (opposing and parallel) thin membranes. The cushion is designed to fit into a slot whereby the pressure exerted on the membranes (by fluid in the tube) is sensed by opposing and parallel sensors mounted adjacent to the slot. The slot is sized to closely fit the cushion in a depressurized state so that even slight pressure variations can exert small dimensional changes in the membranes which can then be detected by the sensors. One disadvantage of this arrangement is that if a user inadvertently connects a liquid supply to the tube set (i.e. "spikes the bags") before inserting the cushion into the slot, the pressure of the liquid will have expanded the membranes to a point where the cushion will not fit into the slot.

It is also noted that some prior art peristaltic pumps operate only during the time they are below or at the pressure level called for by the control system. Once this pressure is reached, the pumps stop turning. In certain applications it would be desirable to keep the pump turning at all times to improve response time and to enable users to see that the pump is still working.

It is accordingly an object of this invention to produce a pressure transducer that may easily sense pressure in a way to avoid the disadvantages of the prior art.

It is also an object of this invention to produce a simple, disposable tubing cassette for use with a peristaltic pump roller assembly.

It is another object of this invention to produce a peristaltic pump roller tubing system which enables a tube to be engaged with a peristaltic pump roller assembly in a simple manual operation.

It is a further object of this invention to enable such a tubing cassette to be disengaged from the peristaltic pump roller assembly in a simple manual operation.

It is another object of this invention to produce a peristaltic pump roller tubing system in which output pressure may be easily measured.

It is still another object of this invention to produce a peristaltic pump roller tubing system which is capable of always providing a mechanical indication that the system is operating.

SUMMARY OF THE INVENTION

These and other objects are accomplished by the preferred embodiment of the system disclosed herein which comprises a tubing system for use with a pump having a peristaltic roller assembly. The roller assembly is rotatable in a plane parallel to the front panel of the pump housing and perpendicular to an axis of rotation. While the preferred embodiment is described in terms of a vertical plane of rotation and a horizontal axis, it will be understood that any orientation is feasible. The system comprises a flexible tubing set including a cassette for facilitating the proper positioning of a portion of the tubing set adjacent the pump roller assembly. The cassette comprises a frame which holds a portion of the flexible tube in a loop configuration and enables the loop to be connected to appropriate inflow and outflow tubes. The cassette frame is provided with a pair of tube supports at points spaced apart a predetermined distance and supports a feedback channel in fluid communication with the inflow and outflow tubes. The feedback channel is provided with a pressure transducer designed to operate with a one-sided pressure sensor on the front panel. The feedback channel enables continuous motion of the peristaltic roller assembly and provides a pressure relief mechanism.

In another aspect of the invention the cassette is retained adjacent the one-sided pressure sensor by a latch means comprising a transverse pivot rib which cooperates with the force inherent within the resilient tube looped about the peristaltic roller assembly. This force urges the cassette rotationally about the pivot rib and into engagement with the pressure sensor on the front panel of the housing. A cantilevered anti-rotation mechanism holds the cassette in place even when the pressure transducer may tend to push it away.

In another aspect of the invention the cassette is provided with a structure and loop profile which facilitate one-handed manipulation by a user seeking to engage the tubing set with the peristaltic roller assembly. The loop is pre-formed to maintain a unique "C" or "Ω" shape prior to attachment to the assembly.

The invention also resides in the method of pumping fluid to a surgical site during arthroscopic procedures. The method comprises the steps of providing a tubing set for conveying liquid from a source to a patient and providing a positive displacement pump for operating at various speeds to pump liquid through the tubing set, the pump adapted to be connected to said pump to produce a pump outflow line and a pump inflow line; providing a feedback channel from the outflow line to the inflow line; sensing the pressure in the feedback channel and adjusting the speed of the pump to maintain the pressure in the outflow line within a predetermined range of pressures. The method may further comprise the steps of providing a single flexible pressure transducing diaphragm on the feedback channel, holding the diaphragm contiguous to one or more pressure sensors and using the pressure sensors to sense the pressure exerted by the diaphragm.

The invention also resides in the method of attaching a tubing cassette to a peristaltic pump. The method comprises the step of providing a peristaltic pump roller station having a latching mechanism as described above.

The invention also resides in the method of controlling pump operation as a function of either a set pressure or a set minimum speed. This method comprises the step of comparing the actual motor speed to the set minimum speed and, depending upon the results of the comparison, operating the pump with a pressure based control loop or with a minimum speed based control loop.

DESCRIPTION OF THE PREFERRED EMBODIMENT

Figure 1:
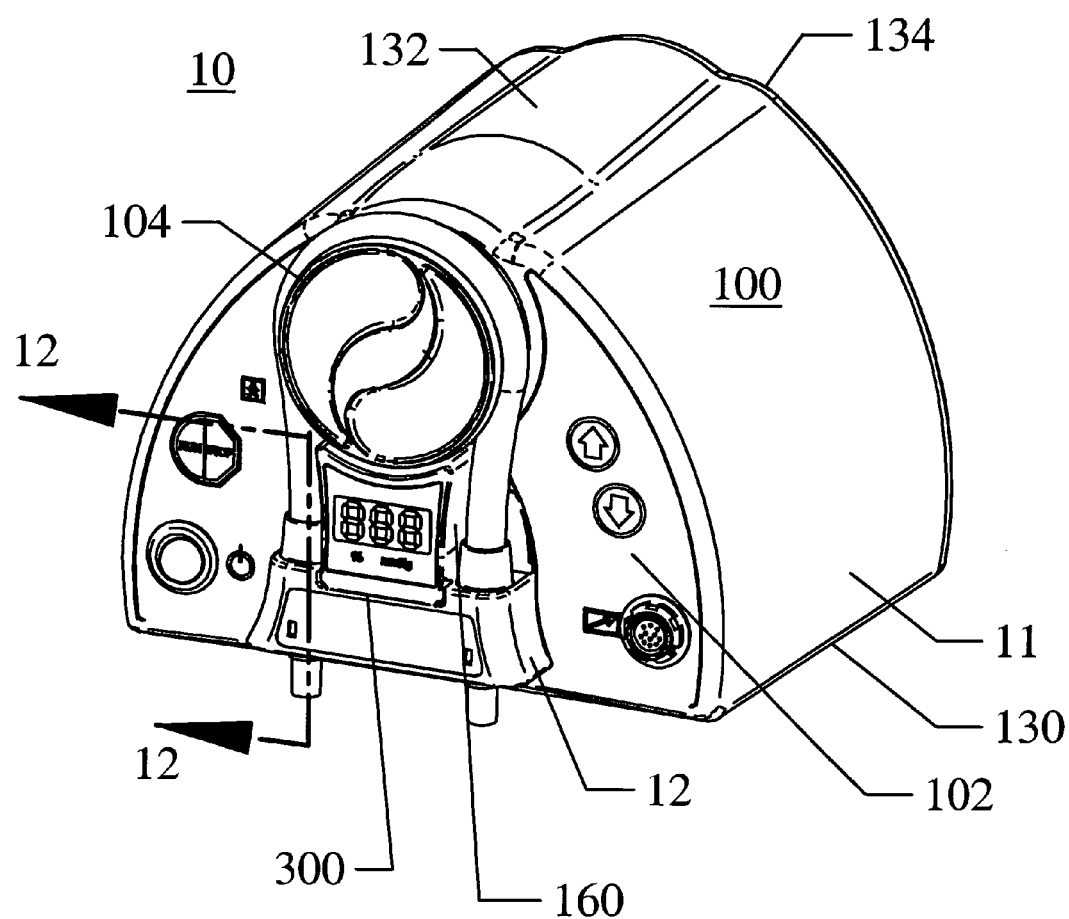
FIG. 1 is a front perspective view of a pump system having a peristaltic pump assembled with a tubing set, all constructed in accordance with the principles of this invention.
Figure 2:
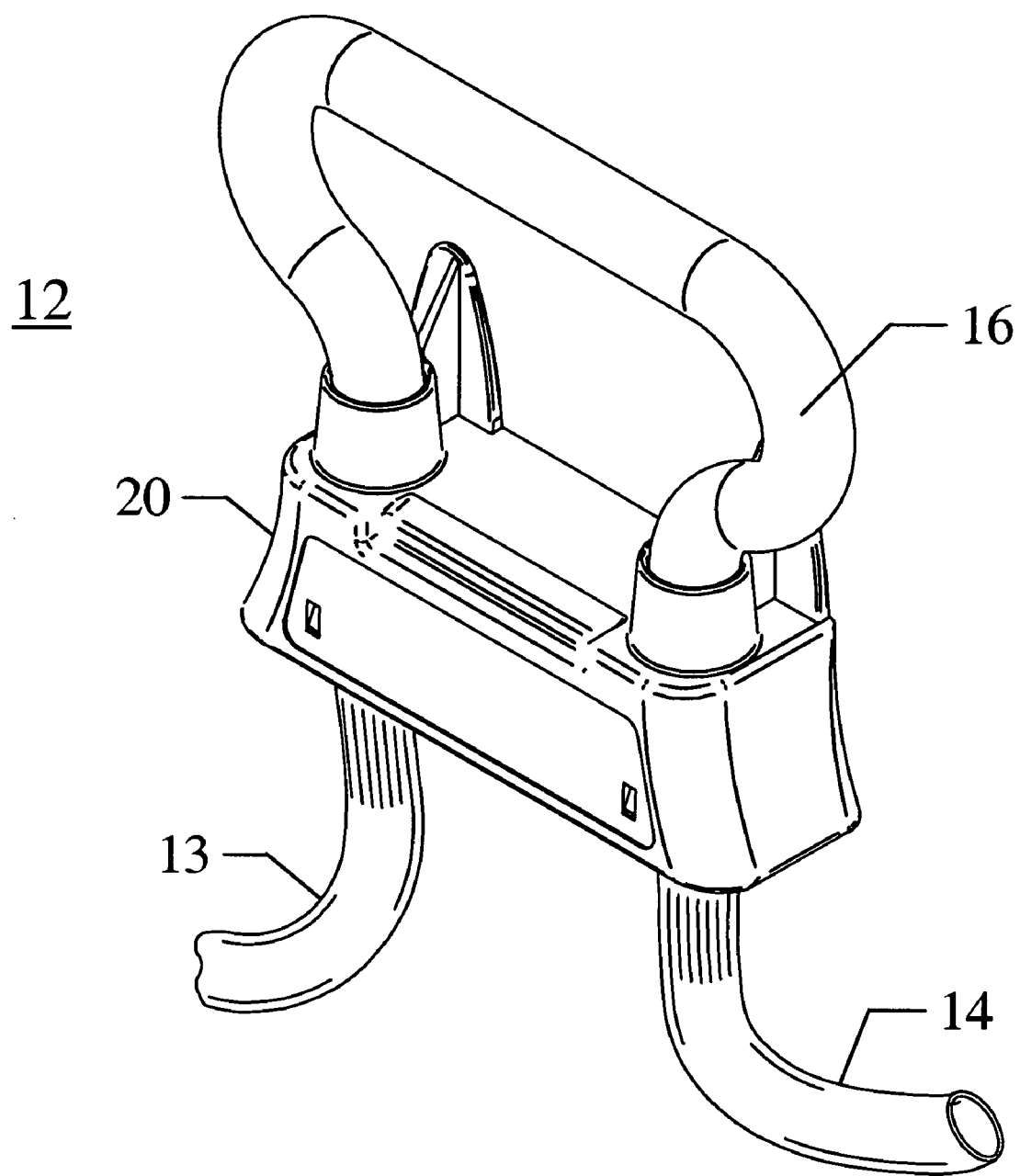
FIG. 2 is a front perspective view of a portion of the tubing set of FIG. 1.

Referring now to FIGS. 1 and 2 there is shown a peristaltic irrigation pump system 10 constructed in accordance with the principles of this invention, comprising pump 11 and tubing set 12. In the preferred embodiment, pump 11 is a peristaltic pump although it will be understood that the invention may be adapted to any positive displacement pump.

As seen in FIGS. 2-11, tubing set 12 comprises an inlet tube assembly 13, an outlet tube assembly 14 and an intermediate looped tube 16, all situated and held by tubing cassette 20. All tubes are preferably resilient and flexible and formed of suitable biocompatible material. As used herein, the term "tubing cassette" broadly means a device for holding at least a portion of the tube, which device is manipulated to facilitate engagement of the tubing set with the pump. Inlet tube assembly 13 may be provided with an appropriate connector (not shown) at its proximal end in order to enable the tube assembly to be connected to a suitable fluid source for use during a particular surgical procedure. (As used herein with respect to tubes, conduits and the like, the term "proximal" will mean that end closest to the fluid source and the term "distal" will mean that end closest to the fluid drain.) The fluid source may be, for example, a conventional bag or bags of saline if the tubing set is to be used to provide irrigation at a surgical site. Similarly, outlet tube assembly 14 may have a variety of connections (luer lock, etc.) at its distal end in order to connect to a variety of instruments to enable the fluid from the fluid source to be used as intended (e.g. irrigation, motor cooling, etc.). Intermediate tube 16 is, in the preferred embodiment, a separate resilient tube attached at each end to a conduit (as will be explained below). However, it will be understood by those skilled in the art that tube assemblies 13 and 14 and intermediate tube 16 could all be formed as one unitary piece.

Figure 13:
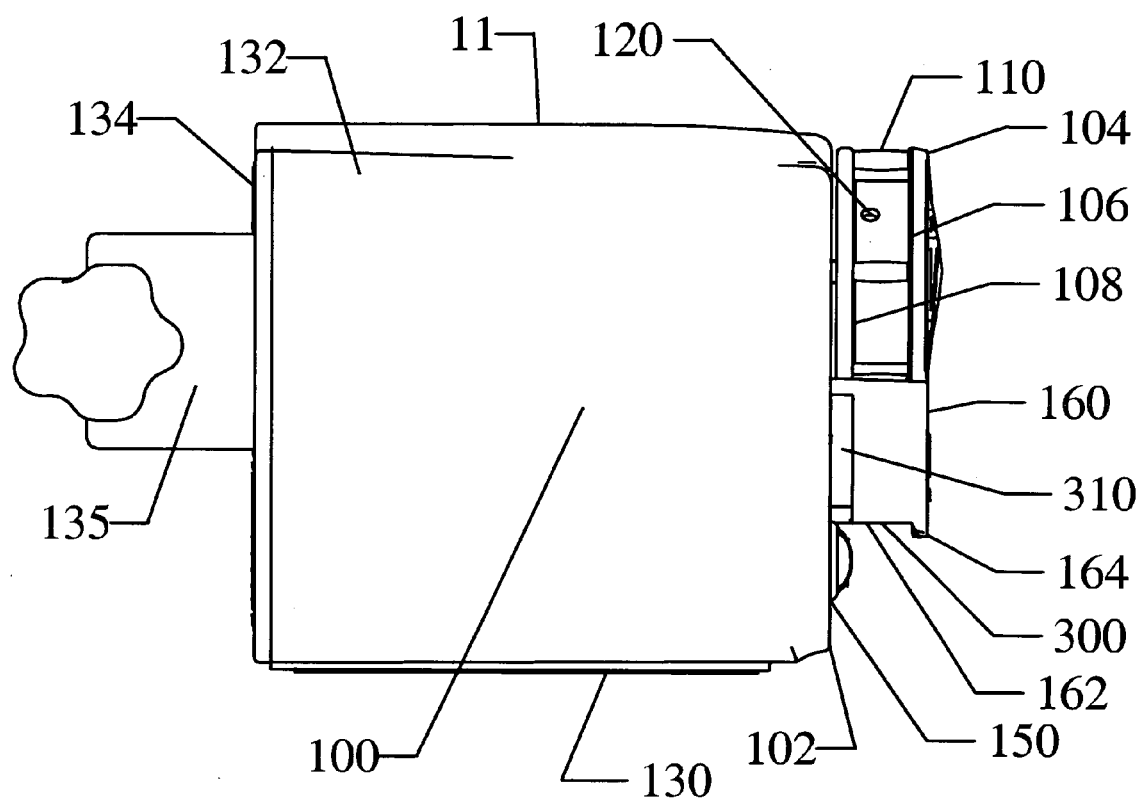
FIG. 13 is a side elevational view of the pump of FIG. 1 shown without the tube set.
Figure 14:
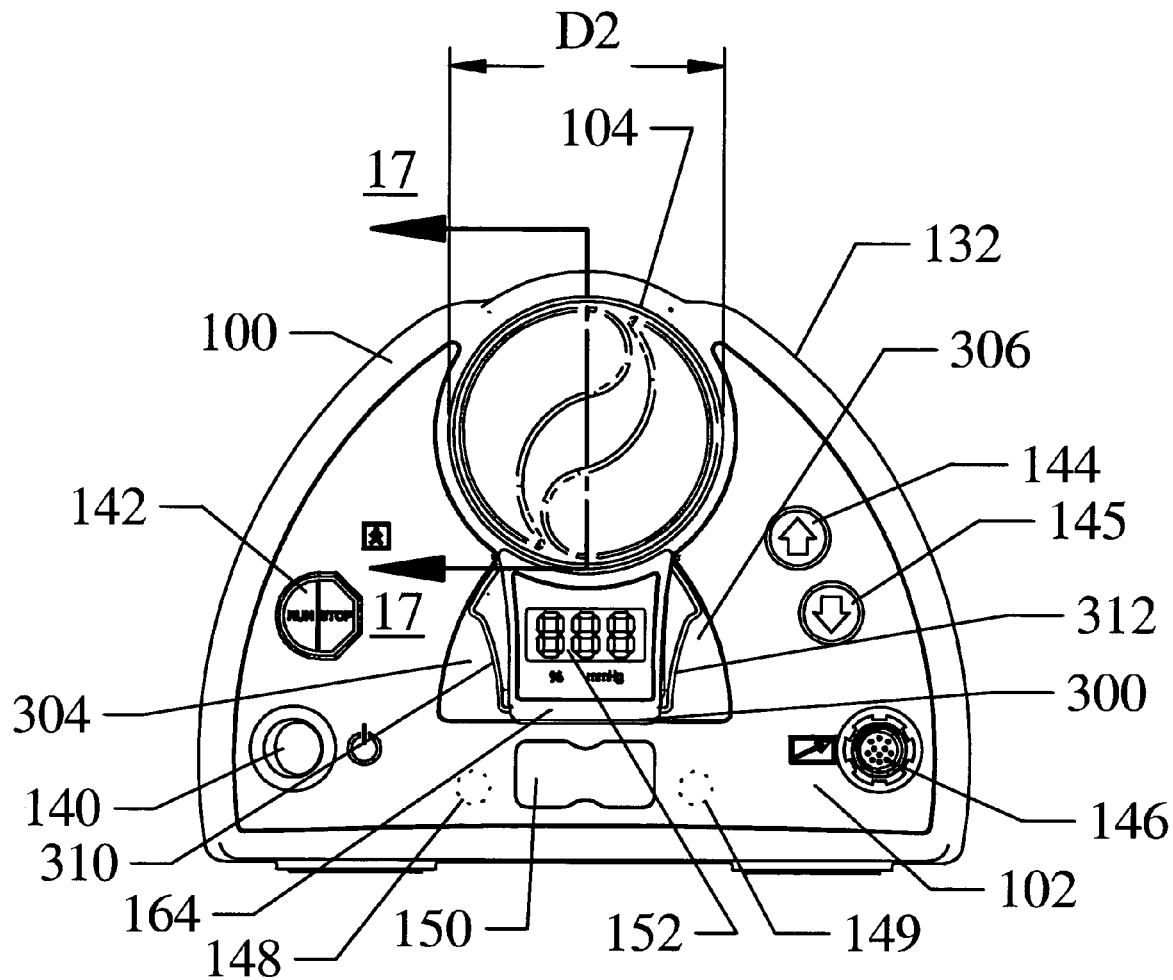
FIG. 14 is a front elevational view of FIG. 13.
Figure 15:
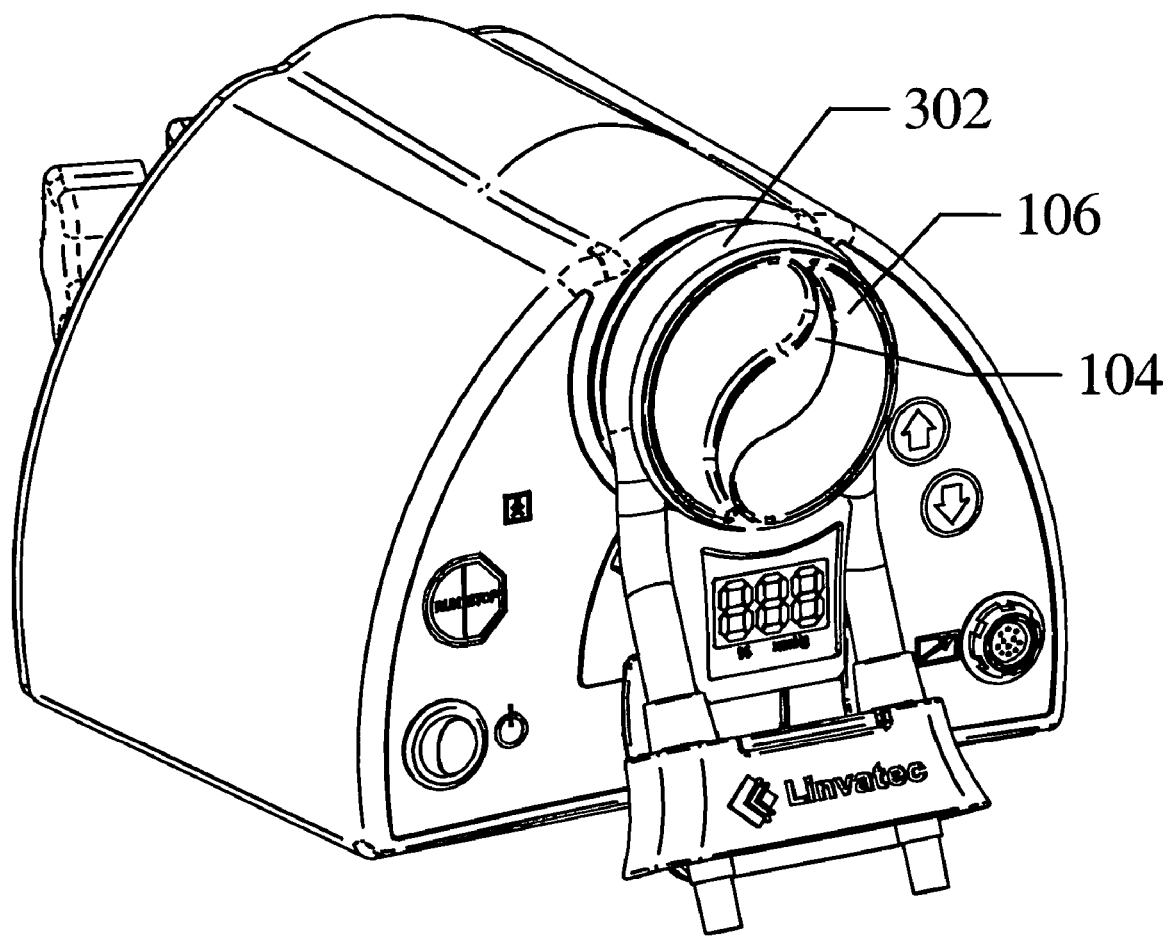
FIG. 15 is a view of FIG. 1 showing a preliminary step in the process of attaching the tube cassette to the pump housing.

Pump 11, best seen in FIGS. 13 and 14, comprises a pump housing 100 which contains a motor (not shown here, but represented in FIG. 18 as motor 1220) having a drive shaft extending through the housing's front panel 102 for driving peristaltic roller assembly 104 in a plane parallel to front panel 102. The left side of roller assembly 104 may be considered a pump inlet and the right side may be considered a pump outlet. Assembly 104 comprises a front plate 106, a rear plate 108 and a plurality of rollers 110 situated on pins 111 secured therebetween. The structure of roller assembly 104 includes a unique hub 120 which enables electrical isolation of the assembly from the pump motor as will be understood below by reference to FIGS. 16 and 17. Pump housing 100 also has a flat bottom surface 130, curved top surface 132, and a rear surface 134 having a pole mounting bracket 135. Front panel 102 lies parallel to peristaltic roller assembly 104 and is provided with various switches to operate the pump control system (not shown) within pump housing 100. Front panel 102 may be flexible enough or thin enough at least in certain spots to enable some switches or controls to be covered and activated by pressure or other stimulus applied directly to the front panel. The control switches comprise power on/off switch 140, a run/stop switch 142, pressure up/down switches 144, 145, remote control connector 146, mode sensing areas 148, 149, pressure sensing area 150. Pressure sensing area 150 may include a plurality of pressure transducers to create redundancy for safety purposes. Display 152 provides information about pump status, sensed pressure, user inputs, set points, etc. Display 152 is situated on the front of projecting cassette support member 160 which has a transverse, downwardly facing support surface 162 and a transverse latching pivot rib 164. As will be further discussed below, pump housing 100 also provides a cassette receiving station 300.

Tubing cassette 20, best seen in FIGS. 2-11, comprises base member 200, cover 202, diaphragm 204 and diaphragm retainer 206. Base or manifold member 200 comprises a frame 207 supporting a pair of parallel conduits 210 and 212 spaced apart a predetermined distance D. Conduits 210 and 212 have lower ends 214 and 216, respectively, for attachment to inflow and outflow tubes 13 and 14, and upper ends 218 and 219, respectively, for attachment to opposite ends 220 and 221 of loop 16. The ends of conduits 210 and 212 may be smooth or barbed. The conduits are situated at opposite ends of a generally rectangular frame 222 having a front surface 224 and a back surface 226. Conduits 210 and 212 have axial lumens 228 and 230, respectively. In the preferred embodiment, base member 200 may be considered a feedback channel means because the conduits and frame 222 have apertures 232 and 234 which provide fluid communication to a pressure relief feedback channel 235 lying along the back surface 226 of the frame between lumens 228 and 230, respectively. Cassette 20 provides support for feedback channel 235, which could even be separate from base member 200.

Figure 4:
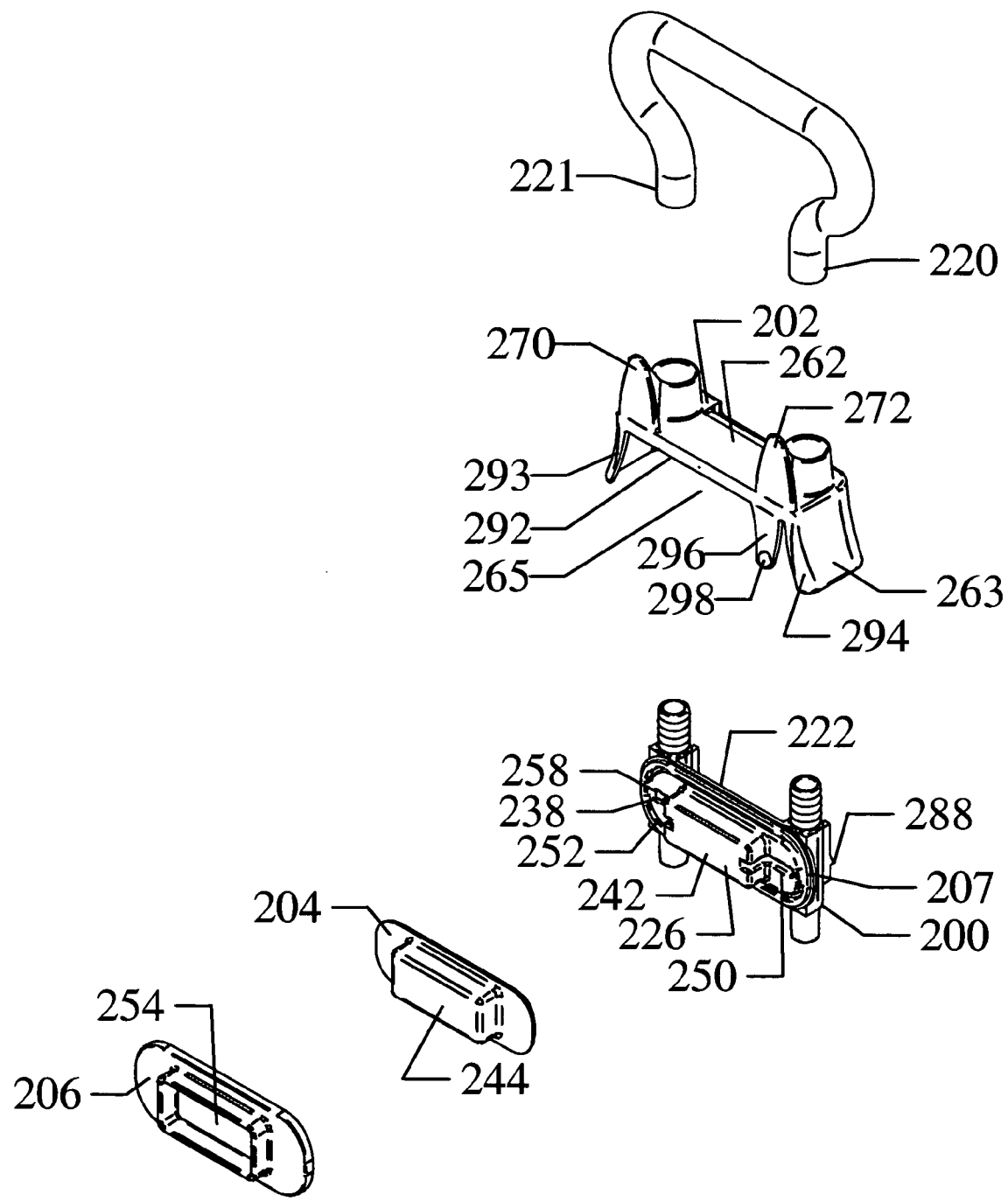
FIG. 4 is an exploded view of FIG. 2 showing a rear perspective view of the various components.
Figure 5:
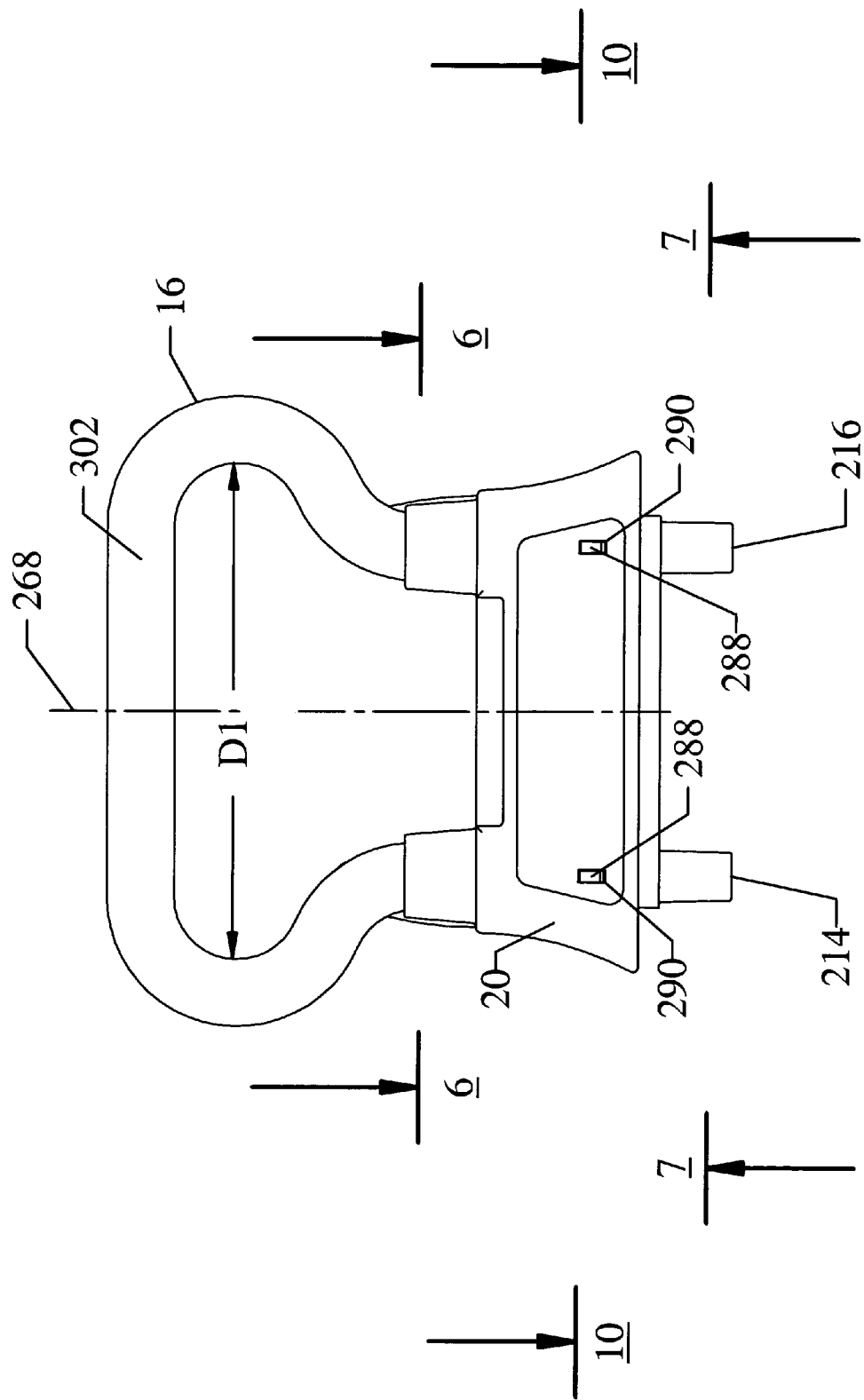
FIG. 5 is a front elevation view of FIG. 2.

Rectangular diaphragm member 204 has a peripheral rib 236 which is received in peripheral groove 238 on back surface 226, thereby covering feedback channel 235 and creating a chamber 240 in fluid communication with lumens 228 and 230. In the preferred embodiment, as best seen in FIG. 4, back surface 226 is raised at 242, and diaphragm member 204 is complementarily shaped at 244, to create a smaller pressure transducer chamber 246. Channels 250 and 252 in back surface 226 provide means for joining apertures 232 and 234, respectively, to the smaller chamber 246. Diaphragm retainer 206 is generally flat and is provided with an aperture 254 to enable raised diaphragm portion 244 to protrude therethrough. Retainer 206 has a peripheral rib 256 which is received in peripheral groove 258 on back surface 226. This enables the outer surface of diaphragm chamber 246 to be placed against the pressure sensing area 150 on the front panel 102 of the housing. It will be understood that diaphragm 204 comprises a one-sided pressure transducer designed to operate with one-sided pressure sensing area 150. As used herein with respect to pressure sensing area 150, the term "one-sided" means that the pressure sensing area is situated on a single surface of the pump housing rather than being situated in a slot or aperture having a finite width. In a sense, the pressure sensing area is unbounded because it extends outwardly from the pump housing surface without limit. The one-sided nature of this pressure sensing area means that a diaphragm or other resilient pressure transducer structure, regardless of whether it is expanded (pressurized) or not, may be placed adjacent the sensing area. If the pressure sensing area had two spaced-apart sides forming a slot of finite width (as in aforementioned U.S. Pat. No. 5,044,203 (Weist et al.)), a diaphragm could only be placed in the slot before the fluid bags are spiked; an expanded diaphragm would not be able to fit. As used herein with respect to diaphragm 204, the term "one-sided" means only one planar wall of chamber 246 is made resilient to direct pressure in one direction.

Base member 200 fits into and cooperates with cover 202 to form cassette 20. Cover 202 is basically a frame intended to receive the base member and it comprises a front surface 260, a top surface 262, side surfaces 263 and 264 and open back 265. Top surface 262 has a transverse groove 266 at its front end, parallel to front panel 102, with a transverse lead-in ramp surface 267. As will be understood below, groove 266 comprises part of a latch means for engaging cassette 20 to secure it at a cassette receiving station. Symmetrically situated on either side of axis 268 of cover 202 are vertically extending anti-rotation members 270 and 272. The anti-rotation members extend vertically above top surface 262 by an amount sufficient to produce a moment arm capable of generating enough force at the distal ends of the members to counteract any tendency of diaphragm 244 to rotate the cassette 20 about front end groove 266.

Figure 3:
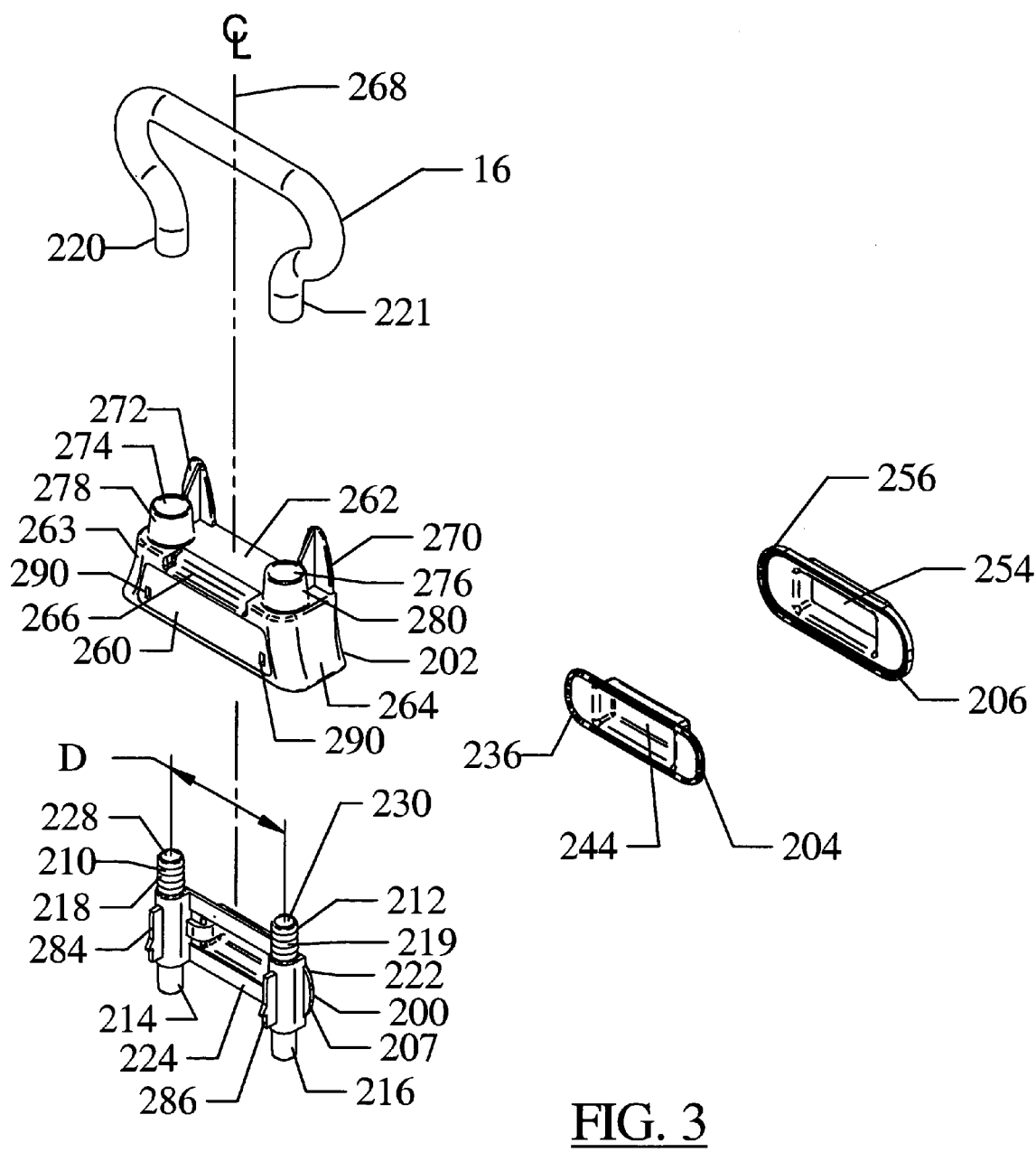
FIG. 3 is an exploded view of FIG. 2 showing a front perspective view of the various components.
Figure 6:
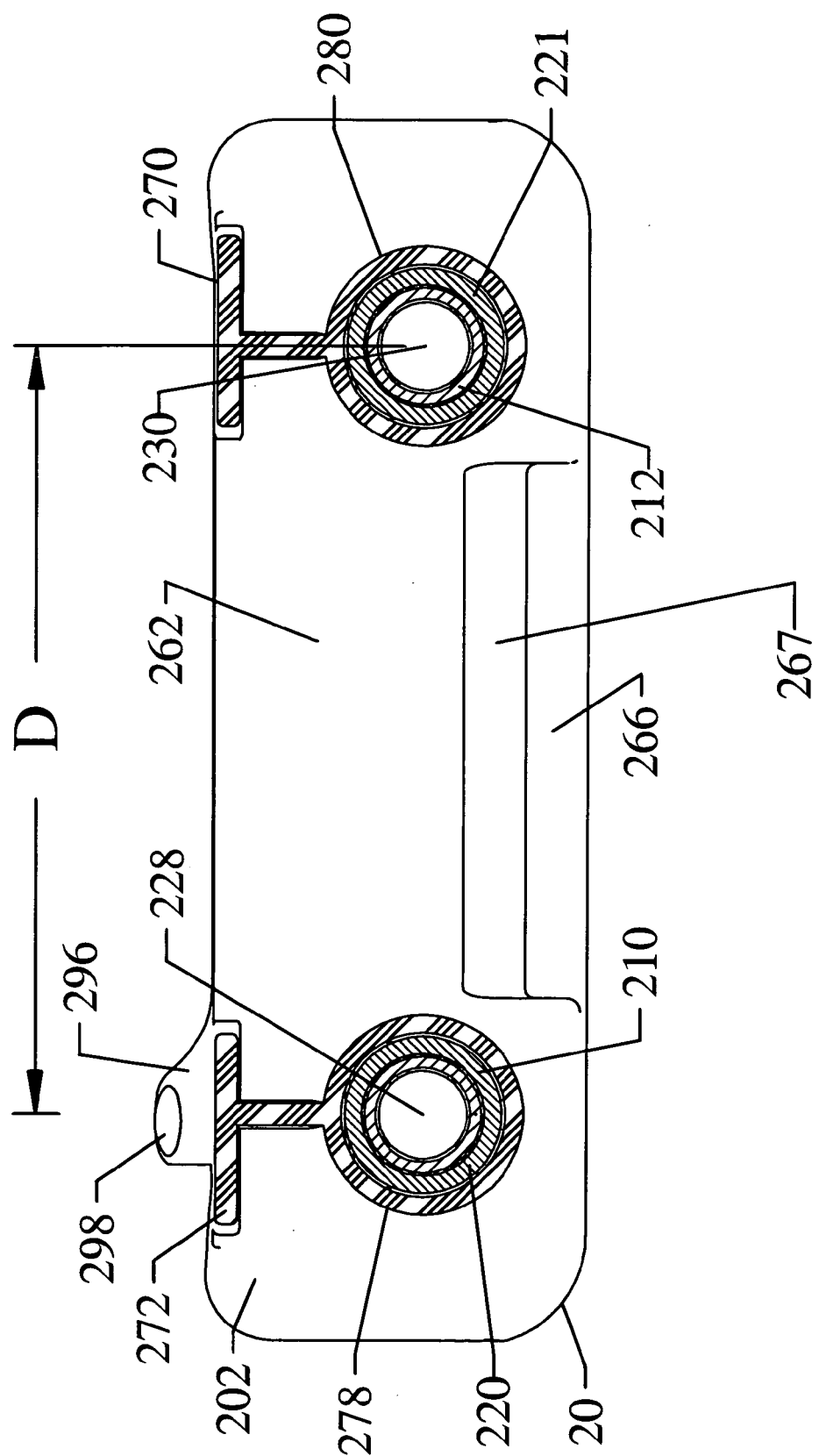
FIG. 6 is a cross-section view of FIG. 5 taken along the line 6-6.
Figure 7:
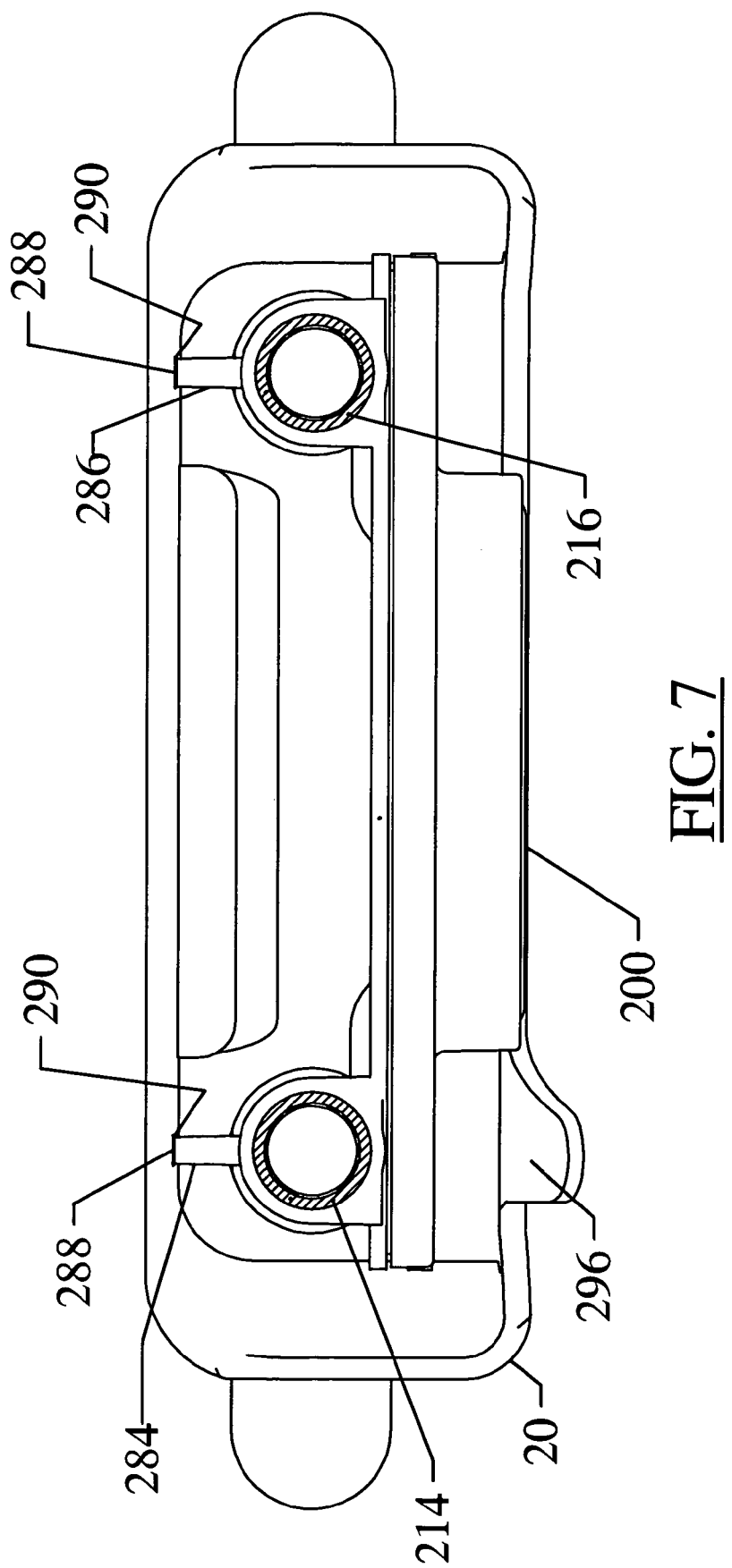
FIG. 7 is a cross-section view of FIG. 5 taken along the line 7-7.
Figure 12:
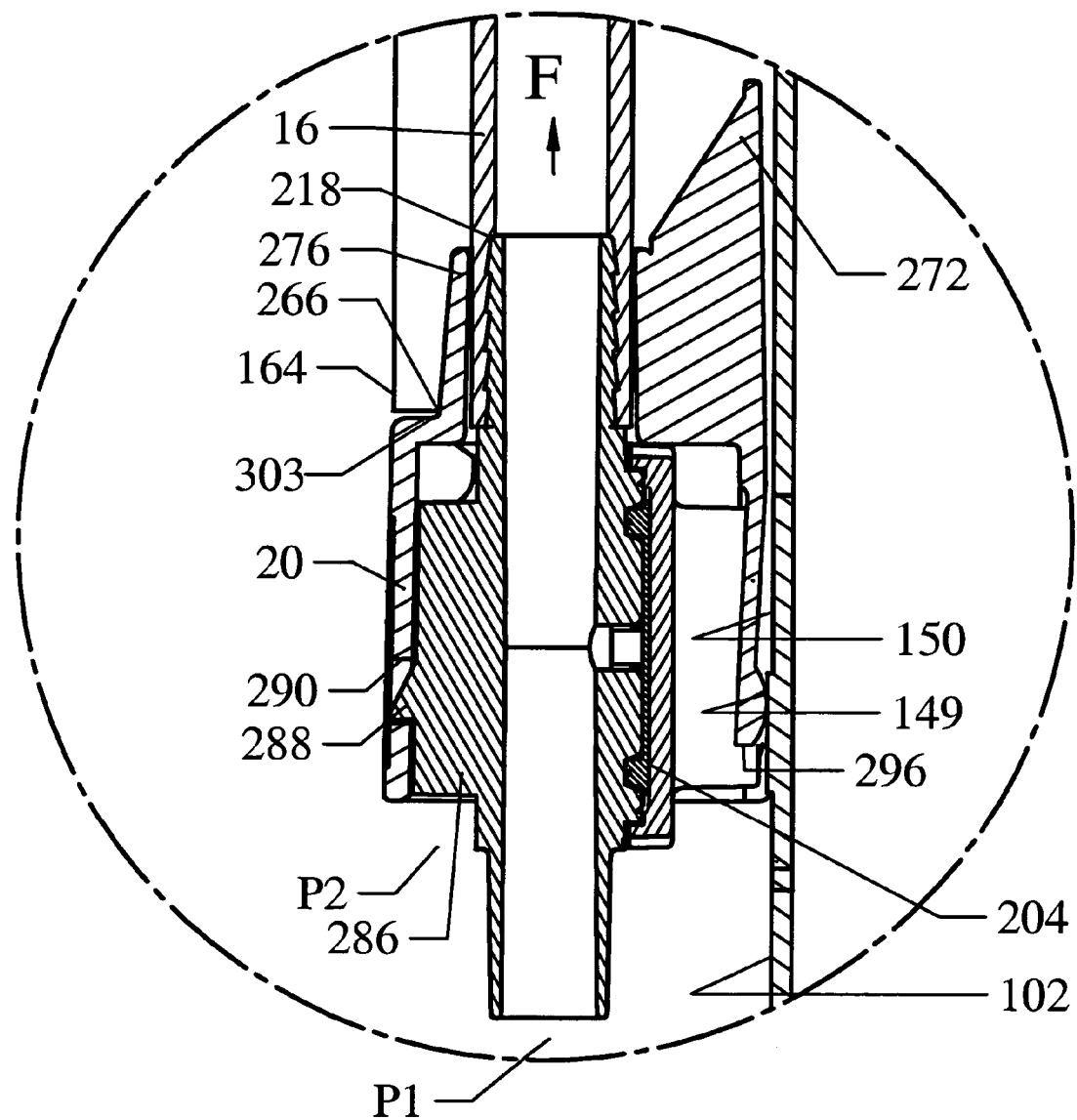
FIG. 12 is an altered cross-sectional view of FIG. 6 taken along the line 12-12, showing in part the pump housing and the deformation of a mode identifying tab by the housing.

In the preferred embodiment, top surface 262 is provided with apertures 274 and 276 defined by bosses 278 and 280, respectively. Bosses 278 and 280 are spaced apart a distance D and serve to secure the ends 220 and 221 of tube 16 to conduit upper ends 218 and 219, respectively. Distance D is preferably small enough to enable cassette 20 to be manipulated one-handedly by users with small hands. The facing annular surfaces of boss 276 and conduit end 219 (and boss 274, conduit 218) may be stepped or serrated to enhance frictional engagement to tube 16. As best seen in FIGS. 3 and 6, cassette 20 is assembled by first placing tube ends 220 and 221 through apertures 274 and 276 and then onto their respective conduit ends 218 and 219. Base 200 and cover 202 are then assembled as shown in FIGS. 3, 5, 6 and 12, thereby capturing tube ends 220, 221 in compression between conduit ends 218, 219 and the interior cylindrical surface of bosses 278, 280. (While only one tube end is shown in FIG. 12, it will be understood that both ends are captured the same way.) In the preferred embodiment the diameter of the inside surfaces of bosses 278, 280 is 0.488 inches (12.40 mm), the outside diameter of conduit ends 218, 219 is 0.383 inches (9.73 mm), and the thickness of tube ends 220, 221 is 0.0675 inches (1.71 mm). Base member 200 may be provided with raised projections 284 and 286 to facilitate its alignment within cover 202. Optional tabs 288 may be provided in base 200 for mating with optional slots 290 in cover 24 to more securely fasten the cassette components together.

Open back 265 of cover 202 is essentially an open area which exposes the outer surfaces of diaphragm retainer and pressure transducer chamber 246. Back 265 is bounded on the top by inwardly extending flange 292 and on the sides by inwardly extending flanges 293 and 294. Cover 202 is also provided with a thin lateral tab or extension 296 (best seen in FIGS. 4, 8 and 9) which extends from flange 292 into the area bounded by flanges 292, 293 and 294. Extension 296 supports on its back surface one or more mode identifiers 298 which are intended to carry some indicia (e.g. white, black or other color dot, bar code, projection, etc.). The indicia may be detected by a sensor (not shown) on the pump console in one or both mode sensing areas 148, 149 to indicate the type of tube set or the presence or absence of the cassette in its proper operating position. This prevents inadvertent operation of the pump and enables the pump characteristics to be matched to the intended surgical procedure.

Figure 8:
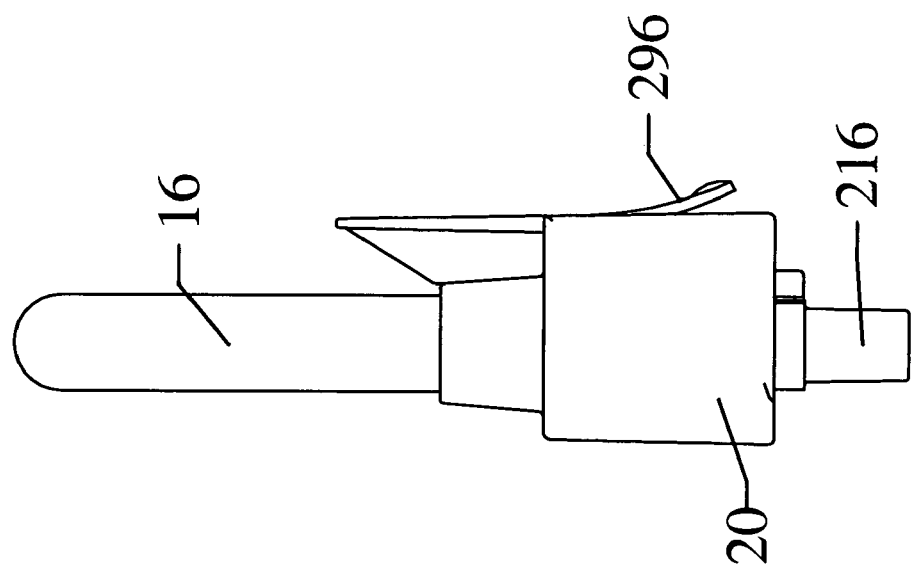
FIG. 8 is a right side elevation view of FIG. 5.
Figure 9:
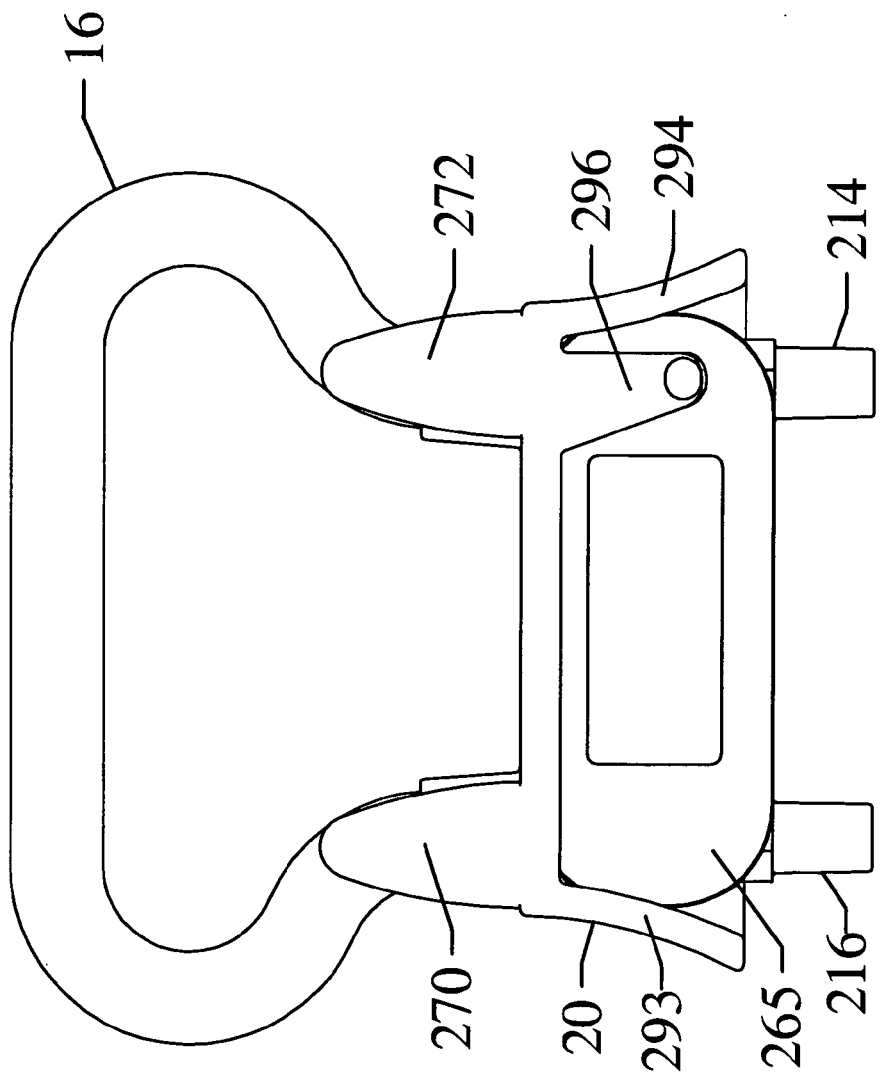
FIG. 9 is a rear elevation view of FIG. 5.
Figure 10:
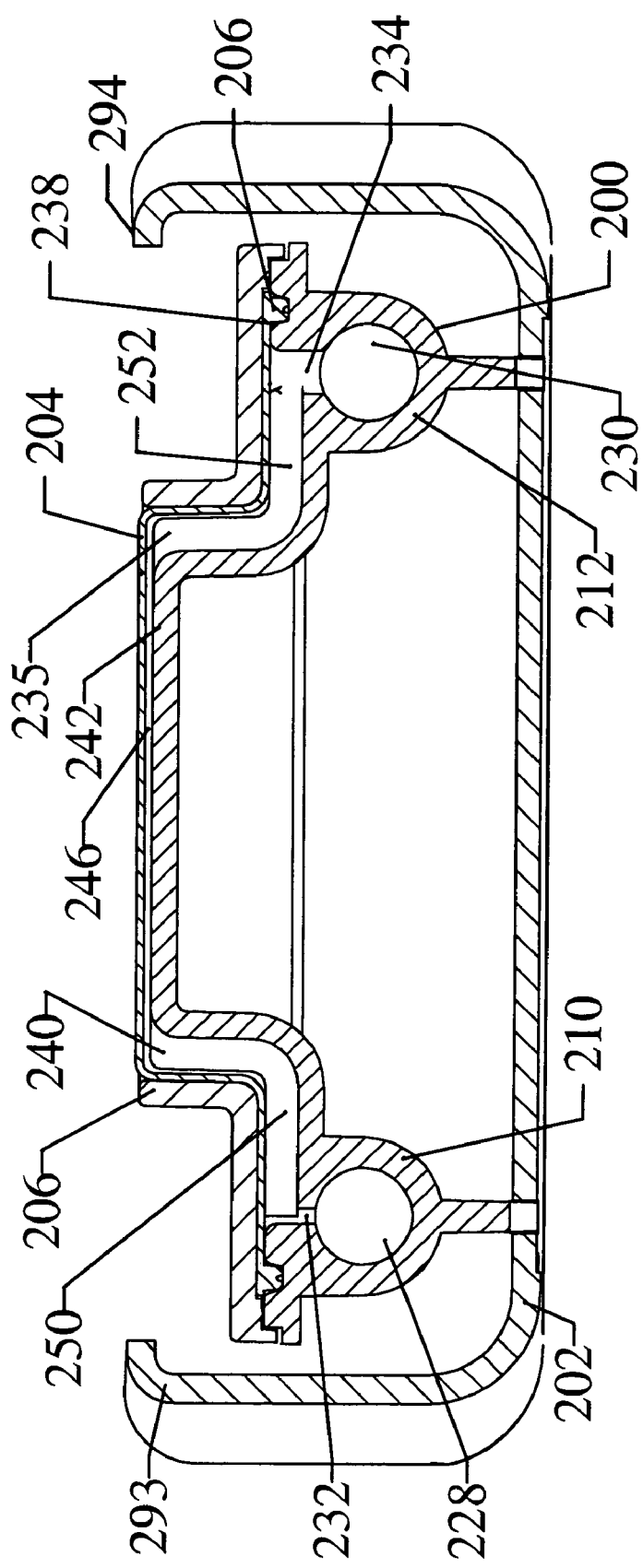
FIG. 10 is a cross-sectional view of FIG. 5 taken along the line 10-10.

Depending upon the type of sensor in areas 148, 149 and mode identifier 298, extension 296 may be resilient or not. That is, if the sensor relies on mechanical pressure, extension 296 may be normally biased rearwardly (as best seen in FIGS. 6 and 8) so that when it is placed against the mode sensing area (best seen in FIG. 12) it will be deformed so that a sufficient amount of pressure will be exerted by the mode identifier to trigger the sensor. If an optical, magnetic, bar code or other type of non-pressure type of sensor is used, extension 296 does not need to be normally biased and may simply lie in the plane of flanges 292-294. While extension 296 is shown only on one side of cover 202, to operate in cooperation with mode sensing area 149, it will be understood that a similar extension could be formed on the other side of axis 268 to operate with mode sensing area 148. Depending upon the functions to be served by mode sensing areas 148, 149 (i.e. type of procedure for which the tubing set is designed, proper cassette placement, etc.) extension 296 may be totally eliminated or an additional extension may be provided simultaneously on both sides of axis 268.

It will be understood that the components of cassette 20 may be molded from polycarbonate or from another suitable plastic or other material having sufficient characteristics to enable their assembly as described herein. Diaphragm member 204 is preferably made of silicone or a similar elastomeric material.

Referring again to FIG. 14, as earlier mentioned, pump housing 100 is provided with a cassette receiving station generally designated as 300. Cassette receiving station 300 comprises a general area adjacent front panel 102 where cassette 20 is designed to be placed to properly engage loop 16 with peristaltic roller assembly 104, to hold cassette 20 in place during pump operation and to properly engage cassette 20 with the pressure sensing and mode sensing area 150 and 148, 149, respectively. When placed at cassette receiving station 300, loop 16 will engage rollers 110, the outer surface of pressure transducer chamber 246 will engage pressure sensing area 150, mode identifier 298 will engage one of the mode sensing areas 148, 149, and latching pivot rib 164 will engage transverse groove 266. Top surface 262 may engage support surface 162 unless, as will be understood below, the rotation of the cassette about pivot rib 164 caused by the resilience of loop 16 is first arrested by the engagement of the cassette with front panel 102. Additionally, vertical anti-rotation members 270 and 272 will lie adjacent vertical support surfaces 304 and 306, respectively.

The method of attachment and use of cassette 20 will be best understood by reference to FIGS. 1, 5 and 13-15. As shown in FIG. 1, in proper operating position, cassette 20 (shown without the tubes 13 and 14 for clarity) is intended to be positioned at the cassette receiving station 300 adjacent the front panel 102 of pump housing 100. Cassette receiving station 300 is adjacent peristaltic pump roller assembly 104 and is bounded by support member 160 situated between roller assembly 104 and pressure sensing area 150. Support member 160 has transverse cassette retaining support surface 162 on its bottom side, and surface 162 has transverse latching pivot rib 164 on its front edge. Pivot rib 164 is adapted to engage groove 266 on the top surface 262 of cassette 20. (Note the locations of the rib and groove could be exchanged.) Lead-in ramp surface 267 is adapted to engage rib 164 and guide it into full engagement with groove 266. To facilitate proper engagement of cassette 20 and tube 16 with the cassette receiving station, tube 16 is preformed into a loop 302 having an internal diameter D1 sufficiently large to enable a user to easily place loop 302 over front plate 106 and onto rollers 110. The preference in the preferred embodiment that the wide of the cassette (effectively distance D) be relatively small must be balanced with the need for a peristaltic roller assembly having a relatively large diameter D2 (FIG. 14). The dimensions and operating parameters (speed, tubing size, etc.) are determined based on fluid flow and pressure required at the worksite. The result of these calculations produces a preferred embodiment in which D2 is greater than D. To facilitate one-handed operation under these circumstances, loop diameter D1 is preferably on the order of distance D2, thereby causing intermediate tube 16 to have a shape approximately like a "C" or "Ω" profile. In the preferred embodiment, the loop is somewhat flattened by a thermoforming process into the "bucket handle" shape shown in FIG. 5. In the preferred embodiment, the diameter D2 of plate 106 is 2.89 inches (73.41 mm) while the loop diameter D1 is 3.475 inches (88.27 mm).

Once loop 302 is placed on peristaltic roller assembly 104, cassette 20 may be pulled down to stretch tube 16 and engage support surface 162 with cassette top surface 262. As this is done, vertical anti-rotation members 270 and 272 will engage vertical support surfaces 304 and 306. Curved lateral centering projections 310 and 312 urge members 270 and 272 laterally in opposite directions to properly position cassette 20 transversely. Pulling cassette 20 below support surface 162 and then slowly releasing it while pushing it toward vertical support surfaces 304 and 306 will automatically position transverse latching pivot rib 164 into transverse latching groove 266 (via lead-in ramp surface 267). As will be understood by reference to FIGS. 12 and 15, when cassette 20 is properly placed at cassette receiving station 300 the inherent resilience of tube 16 will cause peristaltic roller assembly 104 to produce an upward force F in plane P1. This force will tend to rotate cassette 20 counterclockwise about the pivot point 303 (generally the inside edge of groove 266) situated in plane P2 which is displaced a predetermined distance from plane P1. Pivot point 303 is defined by the contact area between latching pivot rib 164 and groove 266.

Figure 11:
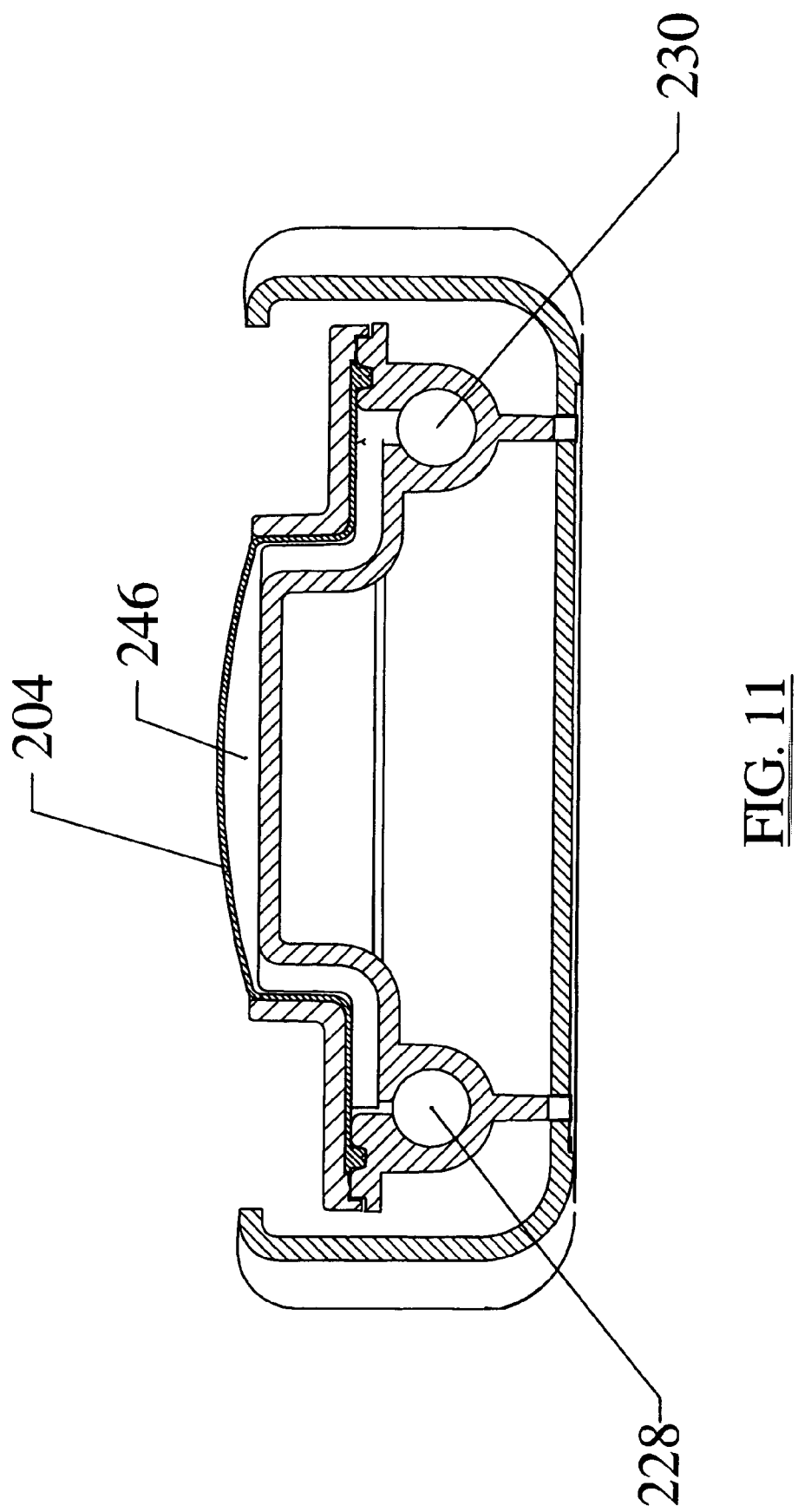
FIG. 11 is a view of FIG. 10 during a portion of the operation of the invention.

When cassette 20 is properly positioned as shown in FIG. 12, the pivoting effect of force F about point 303 urges diaphragm 204, in particular the outer surface of pressure transducer chamber 246 against pressure sensing area 150 on front panel 102. As pressure within chamber 246 builds up, diaphragm 204 will tend to expand in one direction, perpendicular to front panel 102 as shown in FIG. 11. This will cause cassette 20 to be urged clockwise about pivot point 302 as viewed in FIG. 12. This clockwise motion will be countered by anti-rotation members 270 and 272, thus causing the diaphragm to exert pressure against pressure sensing area 150 rather than expand.

The benefit of designing pump 11 with a feedback channel and without a raceway against which tube 16 can be pressed by roller 110 can now be understood. If pressure on the output side of tube 16 increases beyond a certain point, fluid backflow within the pressure relief feedback channel 235 will increase and, relatively simultaneously, the sensed pressure will cause the rotation speed of roller assembly 104 to decrease to a speed just enough to compensate for the pressure loss due to the feedback. Moreover, if pressure at the worksite increases beyond a certain point, the pressure within tube 16 will build up and overcome the elasticity of the tube thereby preventing it from being collapsed by the force of rollers 110. These reactions to high pressure effectively prevents positive displacement of more fluid thereby preventing any further increase in pressure at the worksite.

It will be understood that apertures 232 and 234 are sized and calibrated with pump 11 to provide sufficient flow in feedback channel 235 to limit over-pressure conditions. Aperture 234 on the output side of pump 11 is larger than aperture 232 on the input side to enable aperture 234 to act as a pressure relief mechanism. This also enables a proper degree of diaphragm distention while also providing a large enough fluid path to enable fluid recirculation in the loop comprising loop 16 and channel 235 without increasing pressure at the worksite. In the preferred embodiment of an arthroscopic tubing system, the inside diameter of tube 16 is 0.305 inches (7.75 mm) and the spacing of rollers 110 is such that a suitable volume of fluid is displaced between the rollers (given the fluid flow requirements of the system). The diameters of apertures 232 and 234 are 0.082 inches (2.08 mm) and 0.137 inches (3.48 mm), respectively. Sizes of various components and apertures may vary for other applications. Furthermore, in some applications such as a tubing set intended for supplying irrigating fluid for open surgical procedures, aperture 232 on the input side may be omitted since no feedback is necessary in such applications.

Another beneficial aspect of the invention is that it provides an automatic means for preventing pumping air into the worksite. In the event a fluid source becomes empty inadvertently during use, any air pumped by pump 11 will pass into aperture 232 and 234 and recirculate about the loop comprising tube 16 and feedback channel 235.

Another beneficial aspect of the invention is that it enables the pump to operate continuously after the desired operating pressure is reached. The peristaltic rollers may be rotated slowly to recirculate just enough fluid through the loop comprising tube 16 and feedback channel 235. Not only does this enable a continual visual indication that the pump is operating, but it facilitates a quicker response time when increased flow is desired at the worksite.

While the pump and cassette are shown with tube 16 in a vertical orientation, it will be understood this is only for reference and the system may be used with the component parts oriented horizontally or otherwise. The dimensions of tube 16 and the components of cassette 20 and cassette receiving station 300 are chosen so that when the cassette is properly mounted, tube 16 will be appropriately stretched for proper pump operation.

Figure 16:
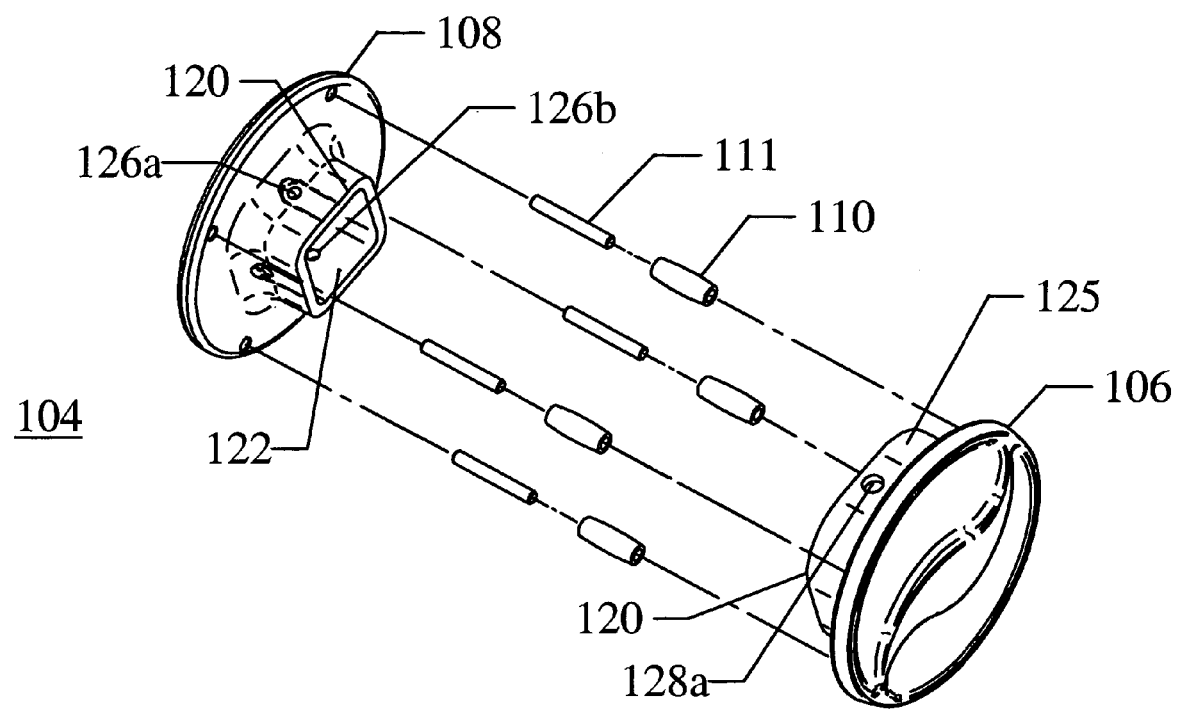
FIG. 16 is an exploded front perspective view of a portion of the pump shown in FIG. 13.
Figure 17:
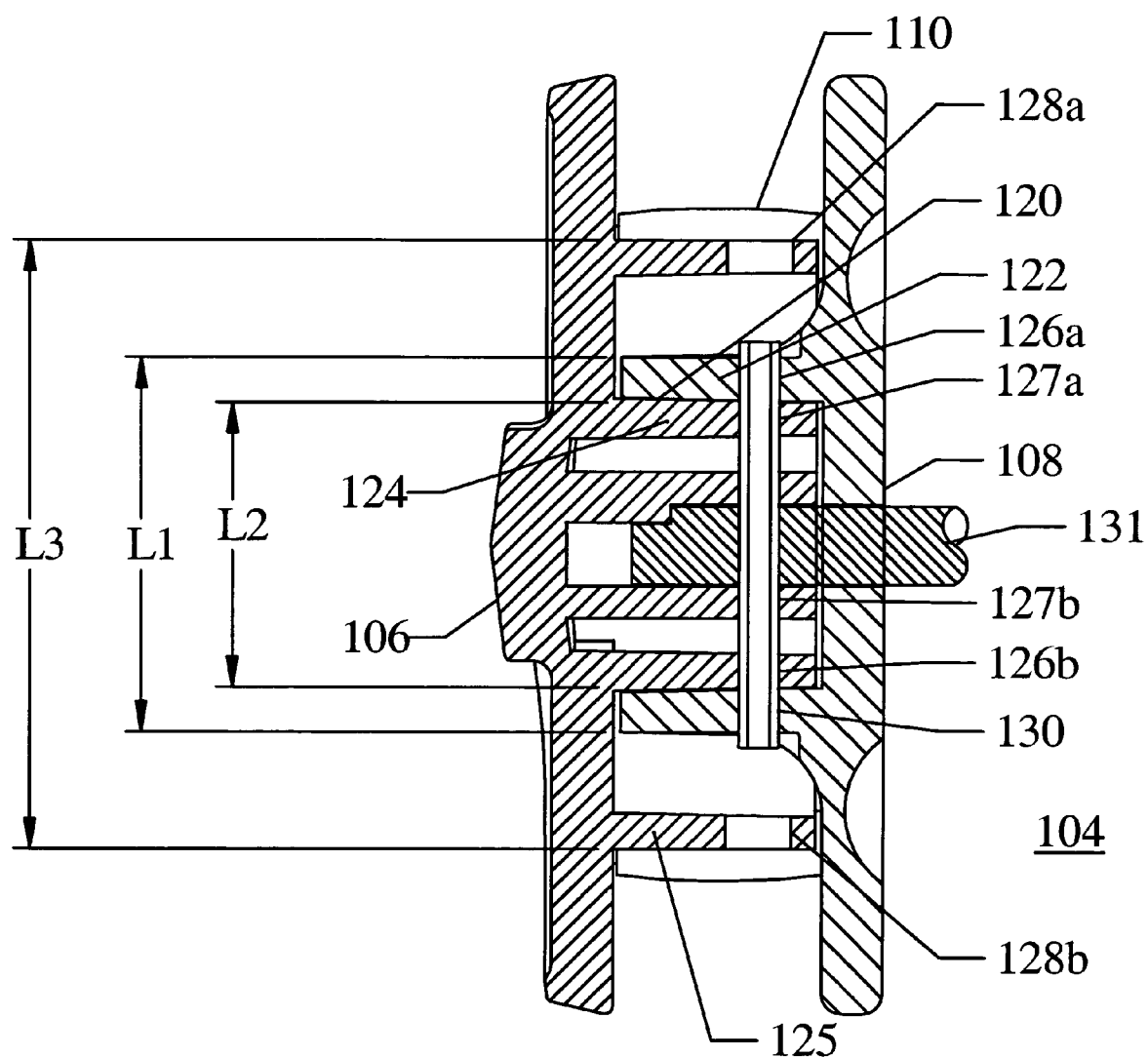
FIG. 17 is a cross-section view of the pump roller assembly of FIG. 14 taken along the line 17-17.

As stated above, hub 120 enables electrical isolation of the pump roller assembly 104 from the pump motor. As seen in FIG. 16, peristaltic roller assembly 104 comprises an electrically isolating hub 120 joining front and rear plates 106 and 108, respectively. Hub 120 comprises an interlocking hub portion 122 situated on rear plate 108, interlocking hub portion 124 situated on front plate 106 and shielding hub 125. In the preferred embodiment, interlocking hub portion 122 has a generally square shape with each side of the square having a length L1. Interlocking hub portion 124 also has a generally square profile with each side of the square having a length L2. Length L1 is greater than length L2 in order to enable hub portion 124 to nest within hub portion 122 (or vice versa) as the front and rear plates 106 and 108 are assembled together using pins 111. Surrounding hubs 122 and 124 is a square sided shielding hub portion 125 having a length L3 on each side. It will be understood that hubs 122 and 124 could be made with any suitable non-circular profile. Shielding hub 125 may be made circular or non-circular. Front plate 106, interlocking hub portion 124 and shielding hub portion 125 are integrally molded together from a suitable electrically non-conductive material. Similarly, rear plate 108 and its hub portion 122 are also integrally molded together from an electrically non-conductive material. Hub portions 122, 124 and 125 have, in each of their (straight) sides, diametrically opposed apertures 126a and 126b, 127a and 127b and 128a and 128b, respectively. A metal or non-conductive transverse pin 130 is inserted through the motor drive shaft 131 and one set of the aligned apertures 126*a*, 127*a* and 128*a* and into aligned apertures 126*b* and 127*b* in order to join front and rear plates 106 and 108 to the motor.

The tubing set 12 described above is preferably utilized for fluid distension during arthroscopic surgical procedures. Similar tubing sets may be used for other similar procedures, although the sizes and dimensions of the various components may be varied as necessary. Furthermore, as mentioned earlier, for certain applications such as irrigation of a worksite during open surgical procedures (using a trumpet valve or other pulsed on/off type irrigating instrument, for example), the tubing set supplying the irrigating instrument (herein referred to as a laparoscopic tubing set) is coded accordingly via mode identifier 298. Such tubing set is generally similar to arthroscopic tubing set 12 but could differ from tubing set 12 by having components of different sizes and dimensions, by omitting the input side aperture 232 and by being controlled differently via a control system that differs from the control system which is suitable for arthroscopic tubing sets. The choice of control system is dictated by mode identifier 298.

Figure 18:
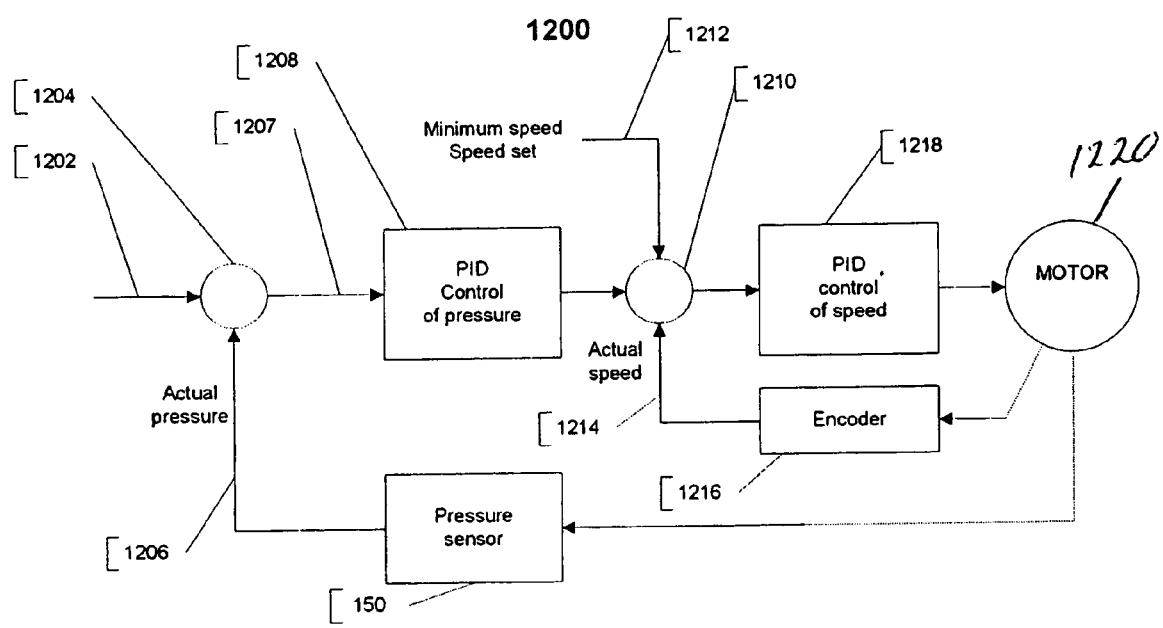
FIG. 18 is a flowchart showing the operation of the control system used to control the pump system constructed in accordance with the principles of this invention.

For an arthroscopic tubing set the mode identifier initiates a protocol which utilizes a control system represented by FIG. 18. This control system is designed to achieve the benefits of the invention as earlier described. For example, there is some benefit to ensuring that the peristaltic pump roller assembly is always rotating above some minimal speed. This provides a visual indication to the user that the pump is operating while minimizing inertia when a higher pump speed is called for. In order to accomplish this, the control system used to operate the pump is a two stage system comprising a nested, dual control loop system 1200, best seen in FIG. 18. In the preferred embodiment, system 1200 incorporates two PID (proportional integral differential) controllers, although other controllers or control loops may be suitable.

The purpose of nesting the PID controllers is to control the peristaltic pump either as a function of pressure, as determined by pressure sensing area 150, or as a function of motor speed, as determined by a speed sensor or encoder (not shown). The transition between the control modes occurs when the pump motor speed drops to a predetermined minimum speed. When the system is turned on, the user is prompted (via display 152) to enter a pressure set point (via up/down switches 144, 145) which will serve as an input on line 1202 to mixer 1204. Mixer 1204 also receives on line 1206 an input from the pressure sensor in pressure sensing area 150 and provides an output control signal on line 1207 to PID controller 1208. The output of PID controller 1208 is provided to a mixer 1210 which also receives an input from line 1212. The input on line 1212 is set to be a predetermined value representative of the minimum speed at which the motor is to run. This speed is chosen in the preferred embodiment to be a relatively low number (on the order of 10 rpm) to provide some visual indication that the motor is operating and also to produce a minimal effect on the pressure within the feedback channel 235. This minimal set point speed (not adjustable by the user) also reduces the inertia which may need to be overcome when the motor is instructed to rapidly increase its speed to maintain set pressure. Mixer 1210 also receives a feedback input on line 1214 from encoder 1216 which monitors the speed of the peristaltic pump motor. The output of mixer 1210 is provided to a second PID controller 1218, the output of which directly controls pump motor 1220.

It will be understood that under normal operation, motor 1220 will result in a pressure at pressure sensing area 150 which is fed back to mixer 1204 to create a closed loop control system. As the pressure increases, the output of mixer 1204 will result in PID controller 1208 eventually decreasing the motor speed as the set point pressure is approached. As long as this motor speed is above the minimum set speed on line 1212, mixer 1210 will provide a signal to PID controller 1218 to run the motor accordingly. When the pressure sensed by pressure sensing area 150 equals the set point, the output of mixer 1204 will be zero thereby instructing PID controller 1208 to stop the motor. This command will be overridden, however, because of the minimum set speed requirement. When mixer 1210 sees that the input from PID controller 1208 would result in a speed less than the minimum set speed on line 1212, the output of mixer 1210 will instruct PID controller 1218 to run the motor at the minimum set speed. In the preferred embodiment, this dual nested control loop system 1200 is accomplished entirely in software. It will be understood, of course, that the same functions could be achieved in hardware.

In a laparoscopic tubing set, feedback of pressure is not important so control system 1200 is not necessary. Therefore, for a laparoscopic tubing set the mode identifier 298 would initiate a protocol including a conventional control loop whereby the user would enter via display 152 a desired maximum flow rate (or percentage value of the maximum rate available). The system will run at this flow rate, or build up pressure to a predetermined value if the irrigator valve is closed. When the valve is opened the conventional control loop will respond to turn the pump motor on or off as required.

It will be understood by those skilled in the art that numerous improvements and modifications may be made to the preferred embodiment of the invention disclosed herein without departing from the spirit and scope thereof.

What is claimed is:

1. In an irrigating fluid positive displacement pump system having a housing with a panel parallel to a peristaltic pump roller assembly having a pump inlet and a pump outlet, inflow tubing to communicate fluid from a source to the pump, outflow tubing to communicate fluid from the pump to a work site, a pressure sensor to sense the pressure of fluid in the outflow tubing and a control system responsive to the pressure sensor to adjust the speed of the pump, the improvement comprising:

a one-sided pressure sensing area situated on said housing, said area containing the pressure sensor;

a tubing set comprising said inflow and outflow tubing and comprising a pressure transducer adapted to be sensed by said one-sided pressure sensing area, said tubing set comprising:

a flexible inlet tube having a proximal end adapted to engage a fluid supply and a distal end;

a flexible outlet tube having a proximal end and a distal end adapted to engage a surgical instrument at a surgical site;

a flexible intermediate tube in operative engagement with the peristaltic pump, said intermediate tube having a proximal end and a distal end, said intermediate tube proximal end secured to said inlet tube distal end and said intermediate tube distal end secured to said outlet tube proximal end;

a cassette means for fixedly holding the ends of said intermediate tube to thereby form a tube loop, said cassette means comprising:

a base member comprising an inlet conduit interposed between said distal end of said inlet tube and said proximal end of said intermediate tube and an outlet conduit interposed between said distal end of said intermediate tube and said proximal end of said outlet tube;

latch means to secure said pressure transducer adjacent to said pressure sensing area, said latch means comprising:

a transverse pivot rib parallel and spaced a first predetermined distance from said front panel, said transverse rib situated between said peristaltic roller assembly and said cassette means;

a transverse groove formed on said cassette means for engaging said transverse pivot rib;

force means acting in a plane parallel to said panel and spaced therefrom a second predetermined distance, said first predetermined distance greater than said second predetermined distance, said force means for producing a force rotationally urging said cassette means about said transverse pivot rib;

support means for preventing rotation of said cassette means about said transverse pivot rib to thereby maintain said tube loop in operative engagement with said peristaltic roller assembly.

2. The improvement according to claim 1 wherein said force means comprises said tube loop in a stretched configuration, whereby force exerted by said peristaltic roller assembly against said stretched loop is directed away from said transverse pivot rib and acts in said plane to hold said cassette means adjacent to said front panel.

3. In a peristaltic pump system having a housing with a panel parallel to a peristaltic pump roller assembly having a pump inlet and a pump outlet, a tubing set comprising:

inflow tubing to communicate fluid from a source to the pump, outflow tubing to communicate fluid from the pump to a work site;

a flexible intermediate tube in operative engagement with the peristaltic roller assembly, said intermediate tube having a proximal end secured to said inflow tubing and a distal end secured to said outflow tubing; and a cassette means for holding the ends of said intermediate tube to thereby form a tube loop, said cassette means comprising:

a base member comprising an inlet conduit interposed between said inflow tubing and said intermediate tube and an outlet conduit interposed between said intermediate tube and said outlet tube, latch means to secure said cassette adjacent said roller assembly, the improvement wherein said latch means comprises:

a transverse pivot rib parallel and spaced a first predetermined distance from said panel, said transverse rib situated between said peristaltic roller assembly and said cassette means;

a transverse groove formed on said cassette means for engaging said transverse pivot rib;

force means acting in a plane parallel to said panel and spaced therefrom a second predetermined distance, said first predetermined distance greater than said second predetermined distance, said force means for producing a force rotationally urging said cassette means about said transverse pivot rib;

support means for preventing rotation of said cassette means about said transverse pivot rib to thereby maintain said tube loop in operative engagement with said peristaltic roller.

* * * * *